United States Patent [19]

McDaniel et al.

[11] Patent Number: 5,780,513

[45] Date of Patent: Jul. 14, 1998

[54] METHOD OF INHIBITING THE RELEASE OF BIOACTIVE IL-1

[75] Inventors: Michael L. McDaniel; Jeanette R. Hill; John A. Corbett, all of St. Louis, Mo.

[73] Assignee: Washington University, St. Louis, Mo.

[21] Appl. No.: 701,574

[22] Filed: Aug. 22, 1996

[51] Int. Cl.$^6$ ................................................ A61K 31/155
[52] U.S. Cl. ................................................ 514/634
[58] Field of Search ................................................ 514/364

[56] References Cited

PUBLICATIONS

Medline Abstract 9 512 7921, 1994, Reimers et al.
Medline Abstract 96132680, 1995, Jo et al.
Dinarello, Modalities for reducing interleukin 1 activity in disease, *Trends in Pharmaceut. Sci.* 14:155–159, 1993.
Dinarello, Interleukin–1, *Adv. Pharmacol.* 25:21–51, 1994.
Corbett et al., Does Nitric Oxide Mediate Autoimmune Destruction of β–Cells?, *Diabetes* 41:897–903, 1992.
Okusawa et al., Interleukin 1 Induces a Shock–like State in Rabbits, *J. Clin. Invest.* 81:1162–1172, 1988.
Fischer et al., Comparison between effects of interleukin–1α administration and sublethal endotoxemia in primates, *Am. J. Physiol.* 261:R442–R452, 1991.
Fischer et al., Initial evaluation of human recombinant interleukin–1 receptor antagonist in the treatment of sepsis syndrome: A randomized, open–label, placebo–controlled multicenter trial, *Crit. Care Med.* 22:12–21, 1994.
Rambaldi et al., Modulation of Cell Proliferation and Cytokine Production in Acute Myeloblastic Leukemia by Interleukin–1 Receptor Antagonist and Lack of its Expression by Leukemic Cells, *Blood* 78:3248–3253, 1991.
Estrov et al., Suppression of Chronic Myelogenous Leukemia Colony Growth by Interleukin–1 (IL–1) Receptor Antagonist and Soluble IL–1 Receptors: A Novel Application for Inhibitors of IL–1 Activity, *Blood* 78:1476–1484, 1991.
Rothwell et al., Involvement of Interleukin–1 and Lipocortin–1 in Ischaemic Brain Damage, *Cerebrovasc. Brain Metab. Rev.* 5:178–198, 1993.
Mrak et al., Glial Cytokines in Alzheimer's Disease: Review and Pathogen Iplications, *Human Pathology* 26:816–823, 1995.
Kimble et al., Persistent Bone–Sparing Effect of Interleukin–1 Receptor Antagonist: A Hypothesis on the Role of IL–1 in Ovariectomy–Induced Bone Loss, *Calcif. Tissue Int.* 55:260–265, 1994.
Bredt et al., Isolation of nitric oxide synthetase, a calmodulin–requiring enzyme, *PNAS, USA* 87:682–685, 1990.
Arend et al., Inhibition Of The Production And Effects Of Interleukin–1 And Tumor Necrosis Factor α In Rheumatoid Arthritis, *Arthritis & Rheumatism,* 38:151–160, 1995.
Henricson et al., An Interleukin–1 Receptor Antagonist Blocks Lipopolysaccharide–Induced Colony–Stimulating Factor Production and Early Endotoxin Tolerance, *Infect. Immun.* 59:1188–1191, 1991.
Mazzei et al., Purification and characterization of a 26–kDa competitive inhibitor of interleukin 1, *Eur J. Immunol.* 20:683–689, 1990.
Seckinger et al., A Urine Inhibitor of Interleukin 1 Activity That Blocks Ligand Binding, *Ann. Inst. Pasteur/Immunol.* 139:1546–1549, 1987.
Bagby et al., Interleukin 1–dependent Paracrine Granulopoiesis in Chronic Granulocytic Leukemia of the Juvenile Type, *J. Clin. Invest.* 82:1430–1436, 1988.
Estrada et al., Nitric Oxide Mediates Tumor Necrosis Factor–α Cytotoxicity In Endothelial Cells, *Biochem. Biophys. Res. Commun.* 186:475–482, 1992.
Michetti et al., Reversible Inactivation of Calpain Isoforms By Nitric Oxide, *Biochem. Biophys. Res. Comm.* 207:1009–1014, 1995.
Gearing et al., Production and Assay of the Interleukins, *J. Immun. Methods,* 83:1–27, 1985.
Remvig, Cellular cytokine bioassays in interleukin–1 quantitation, *Dan. Med. Bull.* 40:255–265, 1993.
Hill et al., Nitric Oxide Production by the Rat Insulinoma Cell Line, RINm5F, Is Specific for IL–1: A Spectrophotometric IL–1 Bioassay, *Analytical Biochemistry,* 236:14–19, 1996.
Dinarello, The interleukin–1 family: 10 years of discovery, *FASTEB J.,* 8:1314–1325, 1994.
Miller et al., The IL–1 β Converting Enzyme as a Therapeutic Target, *Ann. NY Acad. Sci.,* 696:133–148, 1993.
Green et al., Analysis of Nitrate, Nitrite, and [$^{15}$N] Nitrate in Biological Fluids, *Anal. Biochem.* 126:131–138, 1982.
Beckerman et al., Release of Nitric Oxide during the T Cell–Independent Pathway of Macrophage Activation, *J. Immunol.* 150:888–895, 1993.
Stuehr et al., Inhibition of macrophage and endothelial cell nitric oxide synthase by diphenyleneiodonium and its analogs, *FASEB J.* 5:98–103, 1991.

*Primary Examiner*—Zohreh Fay
*Attorney, Agent, or Firm*—Howell & Haferkamp, L.C.

[57] ABSTRACT

A method for the treating an individual afflicted with a disease condition mediated by IL-1 bioactivity is disclosed. The method comprises administering an effective amount of the NOS inhibitor, aminoguanidine, to an individual.

5 Claims, 14 Drawing Sheets

METHOD OF INHIBITING THE RELEASE OF BIOACTIVE IL-1

REFERENCE TO GOVERNMENT SUPPORT

This invention was made with government support under Grants Numbers DK06181, T32, DK07297. The government has certain rights in this invention.

BACKGROUND OF THE INVENTION

(1) Field of the Invention

This invention relates to interleukin-1 (IL-1) and, more particularly, to a method for decreasing the release of bioactive IL-1 by the administration of a nitric oxide synthase inhibitor.

(2) Description of the Related Art

Interleukin-1 (IL-1) conventionally refers to two structurally related polypeptides, IL-1α and IL-1β, that produce diverse biological effects including the induction of fever, sleep, anorexia, hypotension and acute and chronic inflammatory responses. (Dinarello, *Trends in Pharmaceut. Sci.* 14:155–158, 1993, which is incorporated by reference). IL-1 (α and β) is, among other things, a proinflammatory cytokine that serves as a mediator for regulating the immune response. IL-1 is beneficial in such situations as in the stimulation of host defensive responses to microbial invasion and in the promotion of wound healing. Nevertheless, detrimental effects can result from the chronic or excessive production of IL-1. Indeed, a number of pathophysiologic disease conditions are thought to be mediated by IL-1 (Dinarello, *Adv. Pharmacol.* 25:21–51, 1994 which is incorporated by reference). For example, IL-1 production has been implicated in the destruction of β-cells in the islets of Langerhans in autoimmune diabetes (Corbett et al., *Diabetes* 41:897–903, 1992, which is incorporated by reference); the severe hypotension in septic shock syndrome (Okusawa et al., *J. Clin. Invest.* 81:1162–1172, 1988; Fischer et al., *Am. J. Physiol.* 261:R442–R452, 1991; Smith et al., *Am. Soc. Clin. Oncol.* 9:717, 1990; Fischer et al., *Crit. Care Med.* 22:12–21, 1994, which are incorporated by reference); the growth of acute myeloblastic and chronic myelogenous leukemia cells (Rambaldi et al., *Blood* 78:3248–3253, 1991; Estrov et al., *Blood* 78:1476–1484, 1991; Peled et al., *Blood* 78:1172–1177, 1991, which are incorporated by reference); the development of atherosclerosis (Dinarello, *Trends Pharmaceut. Sci.* 14:155–159, 1993, which is incorporated by reference); ischemic brain injury (Rothwell et al., *Cerebrovasc. Brain Metab. Rev.* 5:178–198, 1993, which is incorporated by reference); the progressive degenerative effects associated with Alzheimer's disease and Alzheimer's-like neuropathological changes in Down's syndrome (Mrak et al., *Human Pathology,* 26:816–824, 1995, which is incorporated by reference), and osteoporosis (Kimble et al., *Calcif. Tissue Int.,* 55:260–265, 1994, which is incorporated by reference).

Several isoforms of NOS have been characterized and are classified as constitutive (cNOS) or inducible (iNOS) subtypes based on gene expression and cofactor requirements. The cNOS subtype is localized to the vascular endothelium and brain, is $Ca^{2+}$ and calmodulin dependent, and releases small amounts of NO• in response to physical stimuli or receptor activation (Bredt et al., *PNAS, USA* 87:682–685, 1990, which is incorporated by reference). Expression of the iNOS subtype is induced in a variety of cells, including macrophages, vascular smooth muscle, fibroblasts, and endothelial cells by exposure to endotoxins and cytokines. The iNOS subtype is $Ca^{2+}$ and calmodulin independent, and produces much larger quantities of NO• that are cytostatic and cytotoxic to target cells (Hibbs et al., in Moncada, S., Higgs, E. eds. *Nitric Oxide From L-Arginine: A Bioregulatory System.* New York: Elsevier; pp 189–223, 1990; Rosa et al., *Biochem. Biophys. Res. Commun.* 172:1246–1252, 1990; Stuehret al., *PNAS, USA,* 88:7773–7777, 1991, which are incorporated by reference). Many types of cells constitutively produce a low level of NO• utilizing cNOS, and certain other types of cells and tissues produce large amounts of NO• utilizing iNOS when stimulated by disease, trauma or other stresses. Excess production of NO• has been linked to increased levels of IL-1 bioactivity, yet no causality for this relationship has been established.

A number of approaches for combating the deleterious effects of IL-1 are presently under investigation. These approaches typically involve attempts to reduce the production of IL-1 during the onset of disease or trauma by inhibiting its transcription and translation. Several drugs and other cytokines are known to act in this way by inhibiting the production of IL-1, however, their action in many instances appears to be pleiotropic on the production of other cytokines as well.

One approach to reducing IL-1 bioactivity involves inhibiting proteolytic cleavage of the precursor of IL-1β. Unlike IL-1α precursor, IL-1β requires proteolytic cleavage for optimal biological activity. The enzyme responsible for proteolytic cleavage of IL-1β precursor to its mature and active form is known as the IL-1β converting enzyme (ICE) and is also only found in the cytoplasm of the cell. Inhibitors of ICE have been identified but these are only peptide-based in form and have not been shown to be clinically relevant in reducing the biological activity of IL-1. Furthermore, IL-1α is active as a precursor and does not require processing to be released from IL-1 producing cells. Thus, the approach of blocking proteolytic precursor processing enzymes required for the maturation of IL-1 would be of little value.

Blocking IL-1 receptors has been another alternative for reducing the ability of IL-1 to cause deleterious effects during disease states. Natural peptides capable of binding to IL-1 receptors on target cells have been identified and act to prevent IL-1 binding, which reduces the severity of inflammation and other pathophysiological processes and improves patient survival. This approach has had the disadvantage of requiring the use of recombinant peptide molecules which are unable to be administered orally effectively but instead must be administered by injection. Typically patients have had adverse reactions at the site of injection to these recombinant peptide molecules, and the injections must be repeated over a period of time to achieve beneficial effects (Arend et al., *Arthritis & Rheumatism,* 38:151–160, 1995, which is incorporated by reference).

Alternatively natural peptides have been identified which bind specifically to soluble IL-1 which entirely prevents binding to target cell receptors. These molecules include recombinant peptides consisting of the receptor binding domain specific for IL-1 as well as monoclonal antibodies specific for IL-1. These peptides have the advantage of being able to completely block any IL-1 interaction with receptors in vivo, effectively neutralizing IL-1 altogether. A disadvantage to this approach however is that some IL-1 bioactivity is desirable as it is required for an effective host immune response. Methods which inhibit all IL-1 bioactivity are not desirable and would merit serious consideration before being implemented.

Thus, it would be desirable to have an approach to prevent the deleterious effects of chronic or excessive IL-1 bioactivity which is efficacious, which does not involve treatments lacking in bioavailability, and which does not elicit undesirable side effects.

BRIEF DESCRIPTION OF THE INVENTION

Accordingly, the present invention provides a novel method for treating the detrimental conditions mediated by increased IL-1 bioactivity. The method comprises administering an effective amount of the NOS inhibitor, aminoguanidine. Surprisingly, the increase in IL-1 bioactivity is almost completely inhibited in a time- and concentration-dependent manner by aminoguanidine. This treatment is useful in conditions in which bioactive IL-1 is being produced chronically or in excessive amounts. The terms "treating" or "treatment," as used herein, are intended to mean the diminishing of the magnitude of a disease condition or the prevention of the onset and appearance of a disease condition. The inventors herein have discovered that NO• regulates the bioactivity of IL-1 released from IL-1 producing cells without affecting the amount of IL-1 protein produced within the cell.

Among the several advantages to be achieved by the present invention, therefore, may be noted the provision of a method for treating conditions mediated by IL-1 bioactivity; the provision of a method of treating conditions related to chronic or excessive IL-1 bioactivity; the provision of a method for regulating IL-1 bioactivity which does not alter the synthesis of IL-1 from IL-1 producing cells; the provision of a method for the inhibition of IL-1 mediated NO• formation by NOS; and the provision of a method of treating IL-1 mediated conditions that can be administered orally or parenterally.

DESCRIPTION OF THE PREFERRED EMBODIMENTS

Figure 1B:
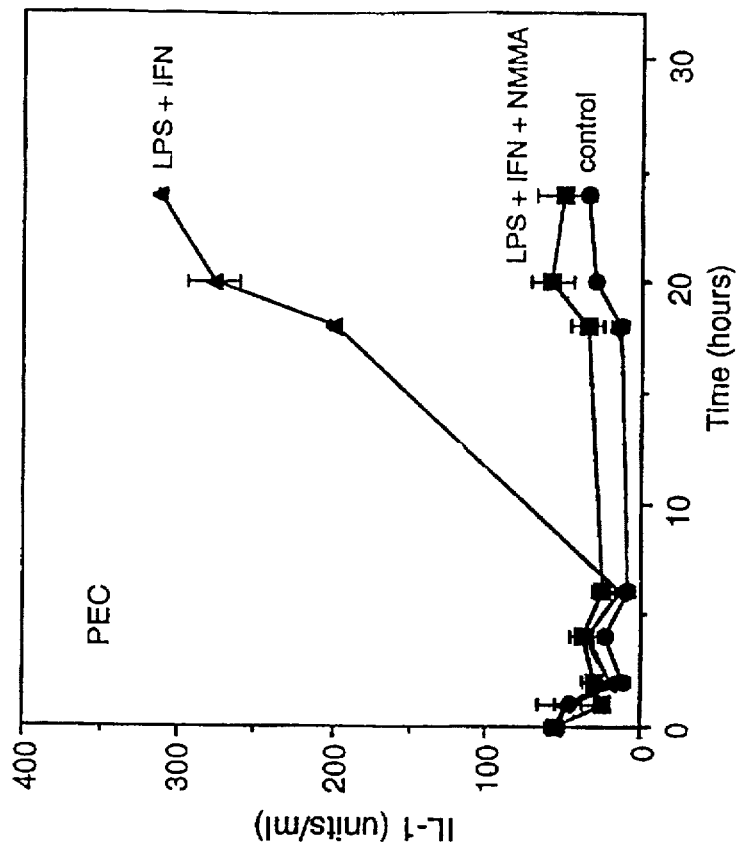
FIG. 1 illustrates the effect of the aminoguanidine analogue, NMMA, in inhibiting the release of IL-1 bioactivity (a) from LPS activated murine macrophages and (b) from murine peritoneal macrophages activated by LPS and IFN.

In accordance with the present invention, it has been discovered that treatment with inhibitors of NOS effectively diminishes IL-1 bioactivity released from IL-1 producing cells. This reduction in IL-1 bioactivity occurs without affecting the amount of IL-1 produced within the cell or processed from IL-1 producing cells. In addition, the effect is concentration dependent and complete abolition of IL-1 bioactivity is achieved at higher concentrations of NOS inhibitors. The method comprises administering aminoguanidine to individuals which serves as the inhibitor to NOS production of NO• and is based upon the discovery that a NOS inhibitor effectively diminishes the bioactivity of IL-1 without affecting the levels of IL-1 protein synthesized or processed by IL-1 producing cells. Aminoguanidine is the preferred NOS inhibitor for use in the present invention. Other less preferred NOS inhibitors that are also useful in the present invention are analogues or derivatives of aminoguanidine such as $N^G$-monomethyl-L-arginine (NMMA), N,N'-diaminoguanidine, methylguanidine, and 1,1'-dimethyl guanidine. A significant distinction of aminoguanidine compared to the analogues and derivatives above is that aminoguanidine selectively inhibits NO• formation from iNOS whereas the other inhibitors inhibit both iNOS and cNOS.

IL-1 directly affects the host response to disease or injury and is generally considered to be the principle cytokine initiating the primary and strategic response determining the outcome of diseases, particularly inflammatory and infectious diseases. IL-1 enhances the immune response and increases nonspecific resistance to infection. However, acute or chronic IL-1 bioactivity can have severe detrimental properties in patients resulting in debilitating or life threatening conditions that are not directly related to immunologic or inflammatory conditions. For example, high levels of IL-1 found in the blood during sepsis are associated with hypotension, shock and mortality. Methods which block the binding of IL-1 to its receptors or which neutralize IL-1 by binding specifically to IL-1 prevent these symptoms, alleviating the potential deleterious effects associated with these symptoms and reducing mortality. However, IL-1 is required for survival despite its detrimental properties to the host when produced chronically or in excessive amounts.

Blocking systemic levels of IL-1 has proven to be a life-saving clinical strategy, but abolition of IL-1 bioactivity leaves the host with less than optimal immunological defenses. Therefore, inhibiting the bioactivity of IL-1 by administering formulations of aminoguanidine would be advantageous to the host, since the hosts' ability to respond to inflammatory or infections diseases and metabolic disturbances or other conditions mediated by IL-1 would not be impaired. Excessive amounts of IL-1 are typically released from macrophages upon stimulation in response to various environmental stimuli (Mrak et al., *Human Pathology*, 26:816–824, 1995). Aminoguanidine is able to block this through a mechanism of action involving the blockade of iNOS but not cNOS or other cytokines. Thus, only the excessive overproduction of IL-1 bioactivity is alleviated which provides effective treatment of the disease conditions caused by such overproduction of IL-1 bioactivity.

By disease condition, reference is made to aspects, or symptoms of a disease and not necessarily the disease in its entirety. Thus it may be possible that in some patients a particular aspect, symptom or condition might be manifested for a given disease whereas in another patient that aspect, symptom or condition might not be manifested in the same disease. One skilled in the art would readily appreciate that the present invention is directed to the treatment of conditions mediated by overproduction of IL-1 bioactivity. Such conditions include but are not limited to acute hypotensive crises of septic shock induced by Gram negative bacterial infections and Gram positive bacterial toxins, acute hypoglycemia induced by endotoxic shock (Henricson et al., *Infect. Immun.* 59:1188–1191, 1991, which is incorporated by reference), monocytic leukemia (Mazzei et al., *Eur. J. Immunol.* 20:683–689, 1990; Seckinger et al., *Ann. Inst. Pasteur/Immunol.* 139:461–516, 1987; Seckinger et al., *J. Immunol.* 139:1546–1549, 1987, which are incorporated by reference), acute myeloblastic leukemia (Estrov et al., *Blood* 78:1476–1484, 1991, which is incorporated by reference), chronic myelogenous leukemia (Rambaldi et al., *Blood* 78:3248–3253, 1991, which is incorporated by reference), chronic juvenile granulocytic leukemia (Bagby et al., *J. Clin. Invest.* 82:1430–1436, 1988; Dinarello, *TiPS* 14:155–158, 1993, which are incorporated by reference), progressive degenerative effects associated with Alzheimer's disease and Alzheimer's-like neuropathological changes in Down's syndrome (Mrak et al., *Human Pathology*, 26:816–824, 1995, which is incorporated by reference), mediation of bone loss and bone resorption as a result of estrogen deficiency (Kimble et al., *Calcif. Tissue Int.*, 55:260–265, 1994), and other IL-1 induced conditions including fever.

Experimental data describe a role for IL-1 in boosting host natural defense mechanisms, however excess IL-1 bioactivity has been demonstrated to be the major factor in causing deleterious effects in response to disease, suggesting that inhibition of IL-1 bioactivity would prevent these deleterious effects. It has also been demonstrated that some IL-1 bioactivity is required for efficient host immune defense mechanisms, so that inhibition of all IL-1 bioactivity is not desirable. The present invention provides the desired effect of significantly diminishing excess IL-1 bioactivity by treatment with aminoguanidine or related compounds without totally abolishing the desired essential effects of IL-1, therefore reducing or eliminating deleterious conditions brought about by chronic or excessive IL-1 bioactivity.

The present invention can be distinguished from previous approaches as it has no affect on the levels of IL-1 synthesis from IL-1 producing cells, but only significantly diminishes the bioactivity of IL-1. Injury, trauma, or disease states induce the production of bioactive IL-1α and IL-1β, primarily from cells of hematopoietic origin. These peptides are the key mediators in the regulation of the immune response. However, inappropriate expression of IL-1 has been linked to deleterious disease conditions such as are found in patients with arthritis and diabetes, and high levels of IL-1 found in the blood during sepsis are associated with hypotension, shock and mortality. IL-1 research has typically focused on methods for limiting IL-1 synthesis, processing, and secretion, and interactions with its target cell receptors. Since IL-1 is required for an efficient host defense, it is possible that blocking its effects entirely, or reducing its synthesis could cause the host to become more vulnerable to infection or unable to respond effectively to an immunological challenge. The present invention can be distinguished from previous approaches as it has no affect on the levels of IL-1 synthesis, but only significantly diminishes the bioactivity of IL-1.

The major in vivo sources of IL-1 are macrophages and monocytes. Scientists studying IL-1 activity and its effects utilize established cell lines derived from these types of cells. Although the cultured cell lines used in the present work are immortalized lymphocytic cells, murine lymphocytic cells derived from peritoneal washes, or monocytes derived from human blood, one skilled in the art will readily appreciate that any cell that expresses IL-1 can be used in a similar fashion.

It is further possible that the effect of treatment with aminoguanidine or related compounds has some effect on the synthesis or release of newly synthesized IL-1, or some effect on the processing and release of these peptides. Typical secreted proteins are synthesized first as precursors which contain an amino-terminal amino acid sequence referred to as a signal peptide, which is subsequently proteolytically cleaved during the secretion process to release a mature, active protein. However, IL-1α and IL-1β both are synthesized as precursors which are subsequently cleaved to release mature, bioactive forms, yet neither contain sequences related to signal peptides and their mode of release from IL-1 synthesizing cells is unknown. The inventors demonstrate that treatment with aminoguanidine or related compounds does not in fact affect either the synthesis or processing of IL-1α and IL-1β from IL-1 producing cells, therefore dismissing the possibility that the treatment envisioned has any effect on these processes.

While not intended to be bound by any mechanism of action, it is possible that cell death and membrane permeability are required for IL-1 release. It has been established that excessive NO• formation can lead to cell death and membrane permeability. One way of monitoring cell death and membrane permeability is to monitor whole cells and media for the presence of enzymes which are known to be synthesized and localized only to either the cell cytoplasm or some other subcellular compartment, vacuole or organelle. Lactate dehydrogenase is one such enzyme which is common to virtually all cell types and is only found within the confines of intact cells (Estrada et al., *Biochem. Biophys. Res. Commun.* 186:475–482, 1992, which is incorporated by reference). The inventors have determined that LPS induced IL-1 synthesis does not cause membrane permeability or cell death by measuring LDH levels released into the media from LPS stimulated cells, indicating that the mechanism of release of IL-1 bioactivity from LPS activated macrophages is, therefore, not due to cell lysis.

IL-1 converting enzyme (ICE) and calpain are proteases responsible for cleavage of these precursor forms of IL-1. Both enzymes are synthesized in the cytoplasm and remain within the cell. Both enzymes are cysteine proteases and contain free thiol residues. IL-1α is synthesized as a larger precursor which is typically cleaved by intracellular proteases, however the precursor has been shown to be active as well. IL-1β is inactive in its precursor form, and only becomes active when properly processed. NO• is known to readily S-nitrosylate free thiols, which could be a mechanism for the inhibition of bioactivity of IL-1 released in the presence of INOS inhibitors such as aminoguanidine. Michetti et al. (*Biochem. Biophys. Res. Comm.* 207:1009–1014, 1995, which is incorporated by reference) demonstrated that a NO• donor could reversibly inactivate the proteolytic activity of calpain, leading to the assumption that the decrease in IL-1 bioactivity could be due to a modulation in proteolytic precursor processing. However, unprocessed precursors might be detected by pulse/chase and immunoprecipitation, or by ELISA, but not by bioactivity assay. The inventors demonstrate by immunoprecipitation of [$^{35}$S]-methionine labeled IL-1α and IL-1β that the presence of NO• does not affect IL-1α and IL-1β synthesis or precursor processing in LPS stimulated macrophages.

As noted above, the inventors herein have discovered that NO• is altering IL-1 bioactivity. Furthermore, NO• does not stimulate IL-1 bioactivity by modifying the levels or activity of IL-1 inhibitory factors that are co-secreted from LPS activated macrophage cells (particularly IL-1Ra). In addition, the treatment with aminoguanidine or related compounds does not affect IL-1Ra or its production or release from IL-1 producing cells, suggesting that IL-1Ra does not play a role in NO• modification of IL-1 bioactivity.

It is believed that the bioactivity of IL-1 protein is a more useful index of the severity of disease conditions mediated by IL-1 than is the amount of IL-1 produced during disease or trauma. Therefore, treatment of disease conditions manifested by chronic or excessive IL-1 bioactivity by administering effective doses of aminoguanidine or related compounds would inhibit the bioactivity of IL-1 and improve patient conditions and survival rates. Some relevant examples of disease conditions which have been shown to be manifested by chronic or excessive IL-1 bioactivity are monocytic leukemia (Mazzei et al., *Eur. J. Immunol.*, 20:683–689, 1990, which is incorporated by reference), acute myeloblastic leukemia (Estrov et al., *Blood* 78:1476–1484, 1991, which is incorporated by reference), chronic myelogenous leukemia (Rambaldi et al., *Blood* 78:3248–3253, 1991, which is incorporated by reference), chronic juvenile granulocytic leukemia (Bagby et al., *TiPS* 14:155–158, 1993, which is incorporated by reference), progressive degenerative effects associated with Alzheimer's disease and Alzheimer's-like neuropathological changes in Down's syndrome (Mrak et al., *Human Pathology*, 26:816–824, 1995, which is incorporated by reference), mediation of bone loss and bone resorption as a result of estrogen deficiency (Kimble et al., *Calcif. Tissue Int.*, 55:260–265, 1994, which is incorporated by reference), and other IL-1 induced conditions including fever.

Aminoguanidine and other NOS inhibitors, thus, can be used according to this invention to treat diseases or conditions mediated by inappropriate or excessive production of IL-1 bioactivity. Such diseases or conditions can include those that do not involve inflammatory or immunological diseases and/or those diseases or conditions that do involve inflammatory or immunological diseases. The disease conditions within the scope of the present invention are also to be distinguished from disease conditions involving advanced glycosylation end products. Thus, it may be possible that a particular aspect, symptom or condition of a disease is mediated by IL-1 bioactivity while another aspect, symptom or condition that may or may not be concurrently expressed may be mediated by another mechanism such as the production of advanced glycoslyation end products. One skilled in the art would readily appreciate that the treatment of the present invention is intended to be directed to those conditions or symptoms mediated by IL-1 bioactivity. Thus, the present invention reduces or eliminates the severity of disease conditions as a result of chronic or excessive bioactive IL-1 release.

The compositions of this invention may be administered by a number of routes of administration including the oral, sublingual, intranasal, subcutaneous, intramuscular, intravenous, transdermal, intraperitoneal, intrathecal, and rectal routes. The compositions are usually employed in the form of pharmaceutical preparations. Such preparations are made in a manner well known in the pharmaceutical art and comprise from about 1 to about 95 percent by weight of at least one NOS inhibitor.

Such pharmaceutical compositions comprise as active ingredients aminoguanidine or its analogues or derivatives, and a pharmaceutically acceptable carrier. In making the compositions, the active ingredient or ingredients will usually be mixed with a carrier, or diluted by a carrier, or enclosed within a carrier which may be in the form of a capsule or other container. When the carrier serves as a diluent, it may be a solid, semisolid or liquid material which acts as a vehicle, excipient or medium for the active ingredient. Thus the composition can be in the form of tablets, pills, powders, lozenges, cachets, elixirs, emulsions, solutions, syrups, suspensions, aerosols (as a solid or in a liquid medium), ointments containing for example up to ten percent by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art.

For oral administration, the compositions of this invention can be admixed with carriers and diluents molded or pressed into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated in a unit dosage form, each dosage containing an effective amount of aminoguanidine or its analogues or derivatives. The amount of aminoguanidine or its analogues or derivatives will depend its potency and efficacy, but will typically lie within the range of from about 0.001 to about 1000 mg, more usually from about 0.01 to about 500 mg per day. The amount of aminoguanidine or its analogues or derivatives will also depend upon its efficacy of inhibition, but will typically be within the range of from about 0.001 to about 1000 mg, more usually from about 0.01 to about 500 mg per day. The term "unit dosage form" refers to physically discrete units suitable as unitary dosages for human subjects and other mammals, each unit containing a predetermined quantity of active material or materials calculated to produce the desired therapeutic effect, in association with the required pharmaceutical carrier.

The compositions of the present invention are effective over a dosage range that is dependent upon the particular compound used and the effects being treated or prevented. For example, the compositions containing an effective dose of aminoguanidine or its analogues or derivatives will normally comprise dosages that fall within the range of about 0.00002 to about 50 mg/kg of body weight. In treating adult humans, the compositions preferably contain at least one NOS inhibitor in an amount within the range of about 0.0002 to about 20 mg/kg body weight. However, it will be understood that the amount of the compound actually administered will be determined by a physician, in the light of the relevant circumstances including the condition or conditions to be treated, the choice of composition to be administered including aminoguanidine or its analogues or derivatives, the age, weight, and response of the individual patient, the severity of the patient's symptoms, and the chosen route of administration, and, therefore, the above dosage ranges are not intended to limit the scope of the invention in any way.

Preferred embodiments of the invention are illustrated in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. The results obtained in these examples are further shown in Table 1 below and the accompanying FIGS. 1 to 9.

EXAMPLE 1

This example illustrates the time dependent release of IL-1 bioactivity from LPS activated murine macrophages, and the effect of an aminoguanidine analogue, NMMA, in inhibiting the IL-1 release.

The common methods for measuring IL-1 bioactivity, based on IL-1 co-induced thymocyte proliferation, are typically complicated by cross reactivity with other cytokines including IL-2, IL-4, IL-6 and TNF$\alpha$ (Geraing et al., *J. Immun. Methods*, 83:1–27, 1985; Remvig *Dan. Med. Bull.*, 40:255–265, 1993, which are incorporated by reference). Therefore, to facilitate the analysis of IL-1 synthesized from IL-1 producing cells, the inventors previously developed a specific, non-radioactive bioassay for measuring IL-1 bioactivity based on IL-1 induced nitric oxide production by an insulinoma cell line, RINm5F (Hill et al., *Analytical Biochemistry*, 236:14–19, 1996). RINm5F is an insulin secreting cell line purified from a radiation-induced rat islet cell tumor (Dinarello, *FASEB J.*, 8:1314–1325, 1994; Miller et al., *Ann. NY Acad. Sci.*, 696:133–148, 1993, which are incorporated by reference). RINm5F cells respond specifically and linearly to murine and human IL-1$\alpha$ and IL-1$\beta$ in the range of 0.1–1 U/ml (10–100 pg) and do not cross react with IL-2, IL-4, IL-6, IL-9, IL-11, IL-15, TNF$\alpha$, IFN$\gamma$ nor LPS. The response of RINm5F cells to IL-1 can be measured by determining the levels of NO• produced in response to this specific stimulus. Levels of NO• are determined as nitrite released into the media by mixing 50 µl of culture media with an equal volume of Griess reagent (1 part of 0.1% naphthylethylenediamine dihydrochloride in $H_2O$ plus 1 part 1.32% sulfanilamide in 60% acetic acid) in a 96 well microtiter plate (Green et al., *Anal. Biochem.* 126:131–138, 1982). The absorbance at 540 nm is measured using a 96-well automated plate reader, and nitrite concentrations are extrapolated from a standard curve using $NaNO_2$ (Fisher) concentrations between 0.1 and 10 nmol. RAW 264.7 cells, a murine macrophage cell line (Washington University Tissue Culture Support Center) and murine peritoneal exudate cells (PEC) obtained from peritoneal washes of male CD1 mice as described in Beckerman et. al. (*J. Immunol.*, 150:888–895, 1993) are used as sources for LPS induced synthesis of IL-1. Exogenously added LPS induces IL-1$\alpha$ and IL-1$\beta$ synthesis from IL-1 producing cells. All cells were grown or maintained in complete CMRL (CMRL-1066 (Gibco Laboratories, Grand Island, N.Y.) supplemented with 10% heat inactivated fetal bovine serum, 2 Mm L-glutamine, 100 units/ml penicillin, and 100 µg/mL streptomycin), and were incubated for 24 hours after plating at 37° C., 95% air, 5% $CO_2$, and the media (200 µL) was replaced prior to initiation of experiments. RAW 264.7 cells or PEC cells were plated at $2 \times 10^5$ cells in 200 µl total volume into individual wells of microtiter dishes 24 hours prior to initiation of experiments, and the media (200 µl) was removed and replaced with fresh media (200 µl) immediately prior to initiation of experiments.

IL-1 bioactivity was determined by obtaining cell free media from LPS activated RAW 264.7 cells or LPS plus IFN$\gamma$ activated PEC cells and adding 2 µl to RINm5F cells ($2 \times 10^5$ cells in 200 µl; a 1:100 dilution of the spent cell free medium). Concurrently, a standard curve was performed using human IL-1$\beta$ (Cistron, Pine Bluff, N.J.) at concentrations between 0.1 and 1 U/ml (10–100 pg). After incubation for 24 hours at 37° C., 95% air, 5% $CO_2$, the culture medium was collected and nitrite (NO•) levels were determined. Data were µplotted in FIG. 1 (*a*) and (*b*) and IL-1 concentrations in the spent medium were extrapolated from the standard curve.

Alternatively, IL-1 bioactivity was determined using a thymocyte proliferation assay. Cell-free culture media obtained from LPS activated RAW 264.7 cells or PEC cells at a final dilution of 1:100, 1:50 or 1:10 was added to $1 \times 10^6$ thymocytes (200 µl) isolated from 6–12 week old C3H/HeJ mice (Jackson Labs) in RPMI media with 5% fetal bovine serum and 2.5 µM $\beta$-mercaptoethanol and co-stimulated with 1 µg/ml PHA (Muegge and Durham, John Wiley and Sons, 1991, 6.2.1). [$^3$H]-thymidine (1 µCi) was added during the last 6 hours of a 48 hour incubation. The cells were harvested on glass fiber filters and the incorporated label was determined by liquid scintillation counting. IL-1 concentrations were extrapolated from a standard curve performed concurrently using human IL-1$\beta$.

LPS stimulated RAW 264.7 murine macrophage cells and LPS plus IFN$\gamma$ stimulated PEC cells were shown to release bioactive IL-1 into the media (Figure 1(*a*) and (*b*)). RAW 264.7 cells were exposed to 1 µg/ml LPS or to 1 µg LPS plus 0.25 mM NMMA for 24 hours. PEC cells were exposed to 1 µg/ml LPS plus 150 u/ml IFN$\gamma$ or to 1 µg/ml LPS plus 150 u/ml IFN$\gamma$ plus 0.25 mM NMMA for 24 hours. Cell free media was removed at intervals up through 24 hours and stored at −70° C. IL-1 bioactivity was measured by the RINm5F assay as described above.

Figure 1A:
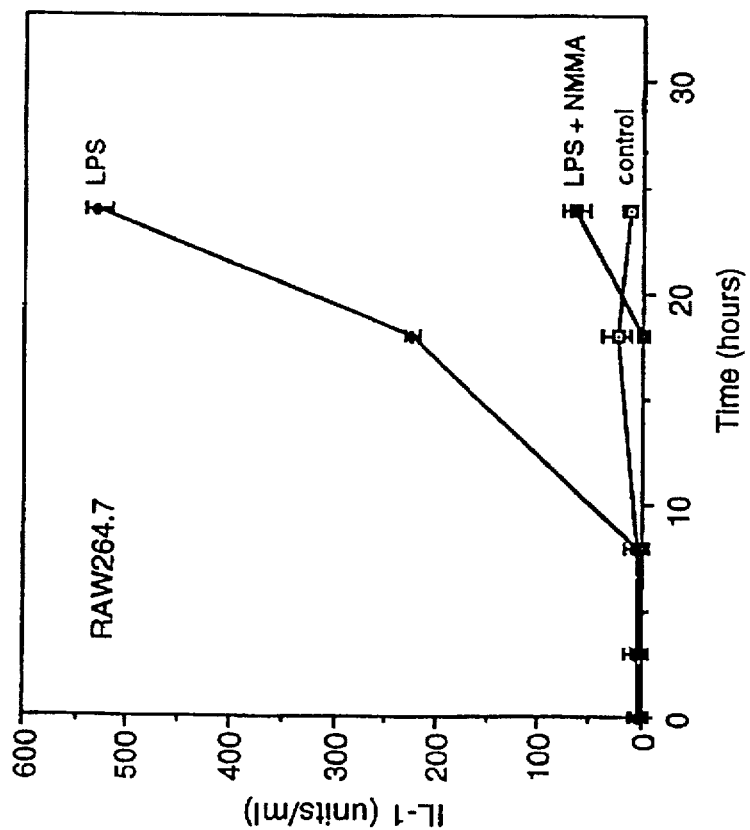

With reference to FIG. 1, LPS stimulated RAW 264.7 murine macrophage cells released bioactive IL-1 which is first detected at 18 hours after addition of LPS and increases to levels 10 fold over non-stimulated control levels at 24 hours (Figure 1*a*). The addition of NMMA to the media along with the addition of LPS almost completely inhibits this time-dependent release of IL-1 bioactivity. The IL-1 bioactivity in the cell-free media was determined at the indicated times by the RINm5F bioassay measuring nitrite levels in response to bioactive IL-1 released into the media from LPS stimulated IL-1 producing cells as described above. As a control to ensure that carry over of NMMA from RAW 264.7 and PEC media did not interfere with the RINm5F bioassay, NMMA was added to the stimulated RAW 264.7 cells at 24 hours, immediately before addition to RINm5F cells. The IL-1 bioactivity in media obtained from LPS and LPS+NMMA at 24 hours stimulated RAW 264.7 cells was identical, indicating that the low concentration of NMMA (1:100 dilution) carried over does not affect NO• production by RINm5F cells. Murine peritoneal exudate cells (PEC) stimulated with LPS plus IFNγ also released bioactive IL-1 in a time dependent manner, and this activity is significantly inhibited by co-incubation with NMMA (Figure 1b).

EXAMPLE 2

This example illustrates the dose dependent inhibition of bioactive IL-1 released from LPS-stimulated RAW 264.7 cells and decrease in NO• levels detected within the media from the same LPS-stimulated RAW 264.7 cells by (a) aminoguanidine and (b) by the aminoguanidine analogue, NMMA.

Figure 2A:
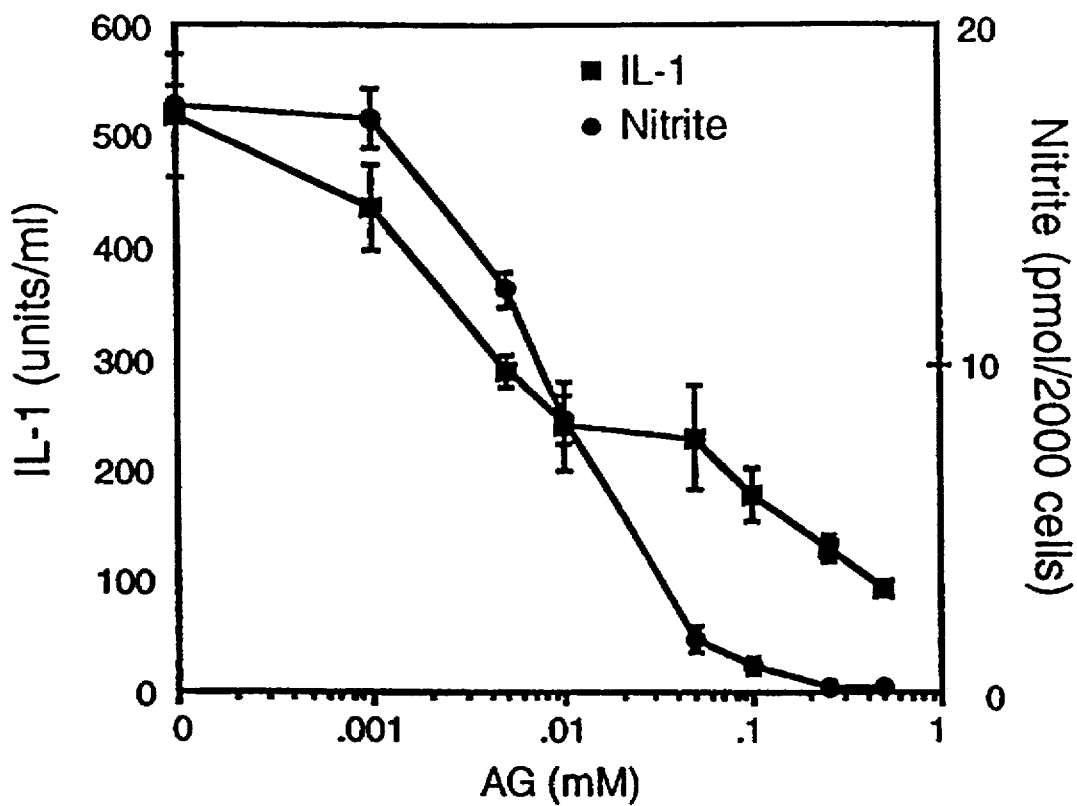
FIG. 2 illustrates the dose dependent inhibition of bioactive IL-1 released from LPS-stimulated RAW 264.7 cells and decrease in NO• levels detected within the media from the same LPS-stimulated RAW 264.7 cells by (a) aminoguanidine and (b) by the aminoguanidine analogue, NMMA.

With reference to FIG. 2, RAW 264.7 cells were co-incubated with 1 µg/ml LPS plus aminoguanidine at concentrations between 0 and 1 mM for 24 hours and media levels of nitrite and IL-1 bioactivity were determined as described above. The chart in FIG. 2(a) illustrates the aminoguanidine concentration dependent inhibition of both release of IL-1 bioactivity and the formation of NO•. The concentration of NO• is shown to decrease in parallel with the decreased bioactivity of IL-1 as aminoguanidine concentrations are increased. This data demonstrates a direct correlation between the levels of NO• and the amount of bioactive IL-1 released from LPS stimulated macrophages. The coordinated decrease in both the levels of NO• and bioactive IL-1 released into the media suggests that the two are somehow related, and perhaps that the decrease could be due to the inhibitory effect of aminoguanidine on NOS, therefore preventing NO• synthesis.

Figure 2B:
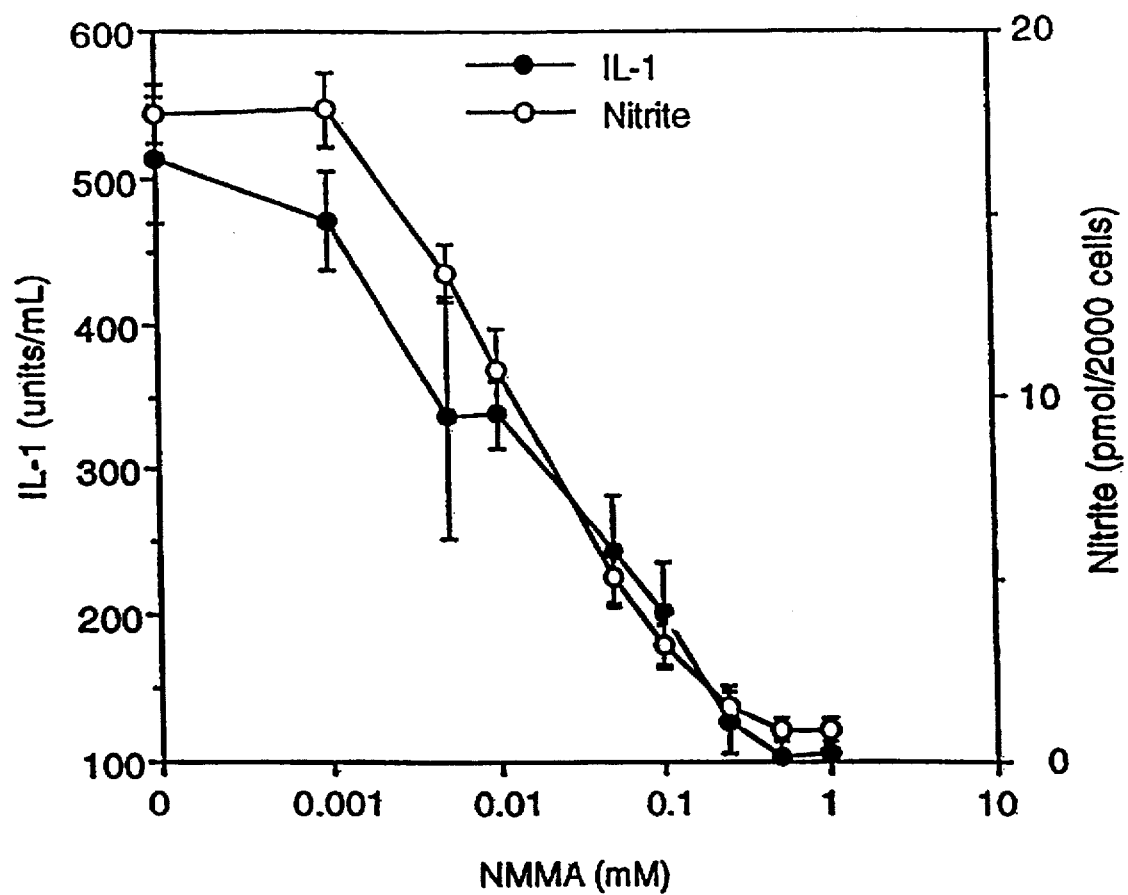

In FIG. 2(b) it is further shown that the aminoguanidine analogue, NMMA, also inhibited IL-1 bioactivity and NO• concentration in the same manner as did aminoguanidine.

EXAMPLE 3

This example illustrates the effects of NOS inhibitors aminoguanidine and iodonium diphenyl (ID) on the release of bioactive IL-1 in comparison to the effect of NMMA.

To determine whether the attenuation of bioactive IL-1 release from LPS stimulated IL-1 producing cells by NMMA is shared by other nitric oxide synthase inhibitors, RAW 264.7 cells stimulated with LPS as above were treated with representatives of two families of NOS inhibitors. Aminoguanidine selectively inhibits iNOS, unlike NMMA which is nonselective in inhibiting both cNOS and iNOS. Another NOS inhibitor, iodonium diphenyl (ID), is also nonselective in that it inhibits both iNOS and cNOS. This substance acts by blocking NADPH and FAD binding sites (Stuehr et al., *FASEB J.* 5:98–103, 1991).

RAW 264.7 cells were exposed to LPS with NOS inhibitors for 24 hours as above. The inhibitor concentrations were 0.25 mM for both NMMA and aminoguanidine, and 0.5 µM for iodonium diphenyl (ID). Controls were performed concurrently to demonstrate that residual NOS inhibitors in the media did not interfere with the IL-1 bioassay as described in Example 1. Media levels of nitrite and IL-1 bioactivity were determined as described in Example 1, above.

Figure 3:
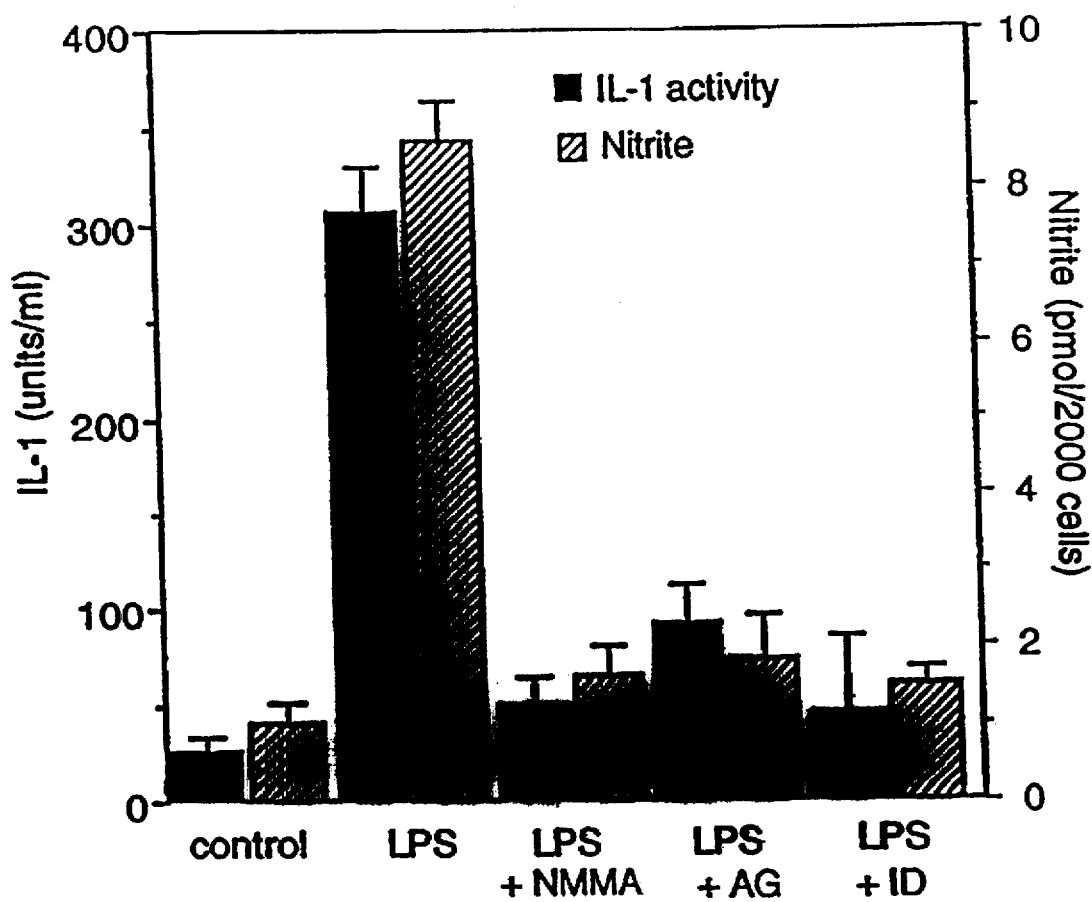
FIG. 3 illustrates the effects of NOS inhibitors aminoguanidine and iodonium diphenyl (ID) on the release of bioactive IL-1 in comparison to the effect of NMMA.

With reference to FIG. 3, aminoguanidine, NMMA, and ID inhibited both release of NO• and IL-1 bioactivity from LPS activated RAW 264.7 cells. This demonstrates the effectiveness of aminoguanidine as an inhibitor of IL-1 bioactivity in comparison to that of NMMA. The ability of both aminoguanidine and NMMA to effectively inhibit NO• formation and release of bioactive IL-1 were virtually indistinguishable. Moreover, these inhibitors effectively inhibited both NOS formation of NO• and diminished IL-1 bioactivity at levels indistinguishable from the effects of the unrelated NOS inhibitor, ID. The data here and from Example 2 demonstrate a direct correlation between the levels of NO• and the amount of bioactive IL-1 released from LPS stimulated macrophages, and appears to suggest that NO• has an effect on the amount of bioactive IL-1 that is observed to be released from LPS stimulated IL-1 producing cells.

EXAMPLE 4

This example shows that the increased levels of bioactive IL-1 in the media from cells stimulated by LPS are diminished by NMMA, and that a NO• donor is able to reconstitute the LPS stimulated IL-1 bioactivity inhibited by NMMA.

In order to determine whether NO• functioned as the mediator that stimulates the release of bioactive IL-1 from macrophages, we determined whether a NO• donor, S-nitroso-N-acetylpenicillamine (SNAP) could reconstitute bioactive IL-1 inhibited by NMMA.

Figure 4:
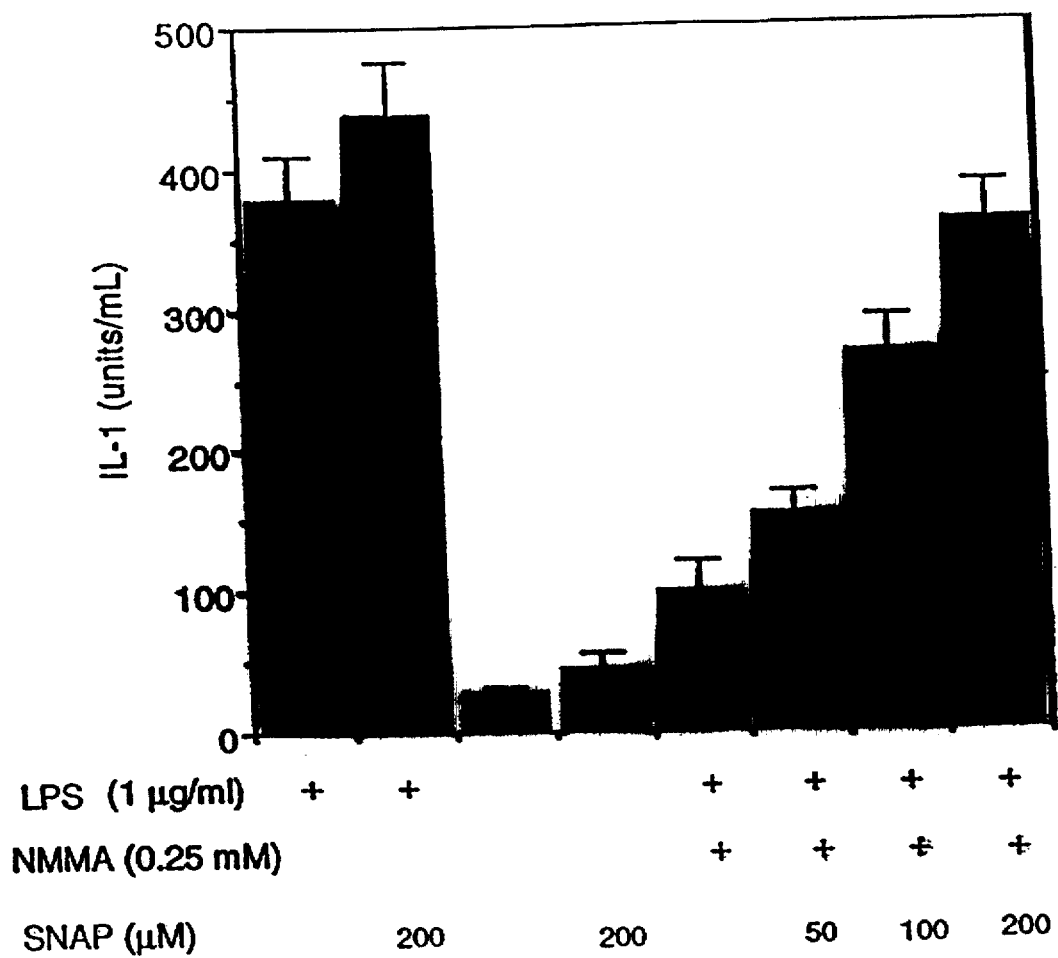
FIG. 4 illustrates increased levels of bioactive IL-1 in the media from cells stimulated by LPS in vitro to produce excess IL-1 are inhibited by NMMA and that a NO• donor is able to reconstitute the LPS stimulated IL-1 bioactivity inhibited by NMMA.

With reference to FIG. 4, RAW 264.7 cells were stimulated with LPS in the presence of 0.25 mM NMMA and SNAP as indicated in FIG. 4 for 24 hours and media levels of IL-1 bioactivity were then measured as described in Example 1. LPS stimulation of RAW 264.7 cells for 24 hours results in a 10 fold increase in media levels of bioactive IL-1 over control levels. LPS stimulated levels of bioactive IL-1 were significantly inhibited by 0.25 mM NMMA. The addition of SNAP reversed the NMMA inhibition of IL-1 bioactivity observed to be released by LPS stimulated cells in a dose-dependent fashion (50–200 µM). These data indicate that inhibitors of NO• formation block the release of bioactive IL-1 and that exogenous NO• donors are capable of reversing the inhibitory effect in a dose dependent fashion. The ability of mechanistically unrelated NOS inhibitors (as in Example 3) to inhibit the release of IL-1 bioactivity, and the ability of NO• donors to reverse this inhibition shows that NO• is the mediator responsible for stimulation of both formation and release of bioactive IL-1 from LPS stimulated IL-1 producing cells.

EXAMPLE 5

This example shows that the increase in IL-1 bioactivity produced by LPS stimulation of murine macrophages was not due to cell lysis.

The cells studied in Example 4 were further evaluated to determine whether the increased IL-1 bioactivity was due to lysis by monitoring lactate dehydrogenase (LDH), which is an intracellular enzyme found within intact mammalian cells and also within the RAW264.7 cells.

To determine levels of LDH in the media, 100 µl aliquots of cell-free supernatant, obtained from RAW 264.7 cells grown as described below, are assayed by incubation with 10 mM pyruvate and 0.1 mM NADH (Sigma) in 0.1M Tris pH 7.5 in a final volume of 1 ml. The oxidation of NADH is measured after 10 minutes by reading the absorbance of the sample at 340 nm. An identical assay is completed to determine the total LDH activity by lysing control cells with 0.1% Triton X-100 for 30 minutes and completing the 10 minute LDH assay. A comparison of the LDH levels found within the media to total LDH levels measured within the control cells allows a determination of LDH release which is expressed as a percent of the total LDH activity observed to be present within the control cell lysate.

With reference to Table 1, RAW 264.7 cells were treated with LPS (1 µg/ml)±0.25 mM NMMA±SNAP for 24 hours in order to stimulate synthesis and release of bioactive IL-1. The culture media was removed and LDH activity, IL-1 bioactivity, and nitrite levels were measured as described. Results are the average of 3 separate experiments containing 3 replicates per condition.

Table 1 illustrates that LPS stimulated increases in IL-1 bioactivity are not due to cell lysis and subsequent release of intracellular IL-1 based on lactate dehydrogenase enzyme activity measurements of the incubation media.

No significant difference in levels of LDH release was detected in the presence of NO• (LPS and LPS+SNAP+ NMMA) or absence of NO• (control and LPS+NMMA). The levels of LDH detected in the media under the various conditions do not correlate with the release of bioactive IL-1 from RAW 264.7 cells. Even though prolonged exposure of RAW 264.7 cells with 200 µM SNAP for 48 hours resulted in significant LDH release, NO• does not appear to be stimulating non-specific release of cytosolic proteins via membrane permeabilization or cell death at 24 hours when release of IL-1 bioactivity is detected (see Figure 1(a)). The absence of NO•-induced cell death at 24 hours was also confirmed by trypan blue exclusion and DNA fragmentation experiments (data not shown).

Thus, the inventors determined that LPS stimulation of the cells to increase IL-1 bioactivity was not due to cell lysis or increased membrane permeability.

TABLE 1

| Treatment[a] | LDH[b](% control) | IL-1 Bioactivity[b] (U/ml) | Nitrite[b] (pmol/2000 cells) |
|---|---|---|---|
| Control | 17.3 ± 1.1 | 27.8 ± 5.2 | 1.5 ± 1.6 |
| control + 200 µM SNAP | 20.1 ± 2.3 | 44.8 ± 11.3 | 53.7 ± 2.1 |
| LPS | 11.5 ± 0.7 | 378.2 ± 31.3 | 19.2 ± 1.0 |
| LPS + 200 µM SNAP | 21.0 ± 1.8 | 437.4 ± 38.4 | 64.9 ± 2.3 |
| LPS + NMMA | 11.7 ± 0.9 | 99.3 ± 21.6 | 1.4 ± 0.6 |
| LPS + NMMA + 50 µM SNAP | 13.0 ± 1.4 | 152.2 ± 15.8 | 15.9 ± 0.2 |
| LPS + NMMA + 100 µM SNAP | 16.4 ± 1.7 | 267.5 ± 25.2 | 28.1 ± 0.6 |
| LPS + NMMA + 200 µM SNAP | 19.0 ± 2.0 | 359.0 ± 29.3 | 55.4 ± 1.3 |

[a]Treatments of RAW264.7 cells (4 × 10[5] cells/400 µl) were LPS (1 µg/ml), NMMA (0.25 mM), and SNAP (50, 100 or 200 µM as indicated).
[b]Results are reported as mean ± SEM, n = 3; LDH, lactate dehydrogenase activity, represents the level of activity in the media in comparison to the total amount detected in cells and media samples combined

EXAMPLE 6

This example illustrates the effects of NMMA and NO• on the amount of IL-1 protein released by LPS stimulated RAW264.7 cells.

Figure 5:
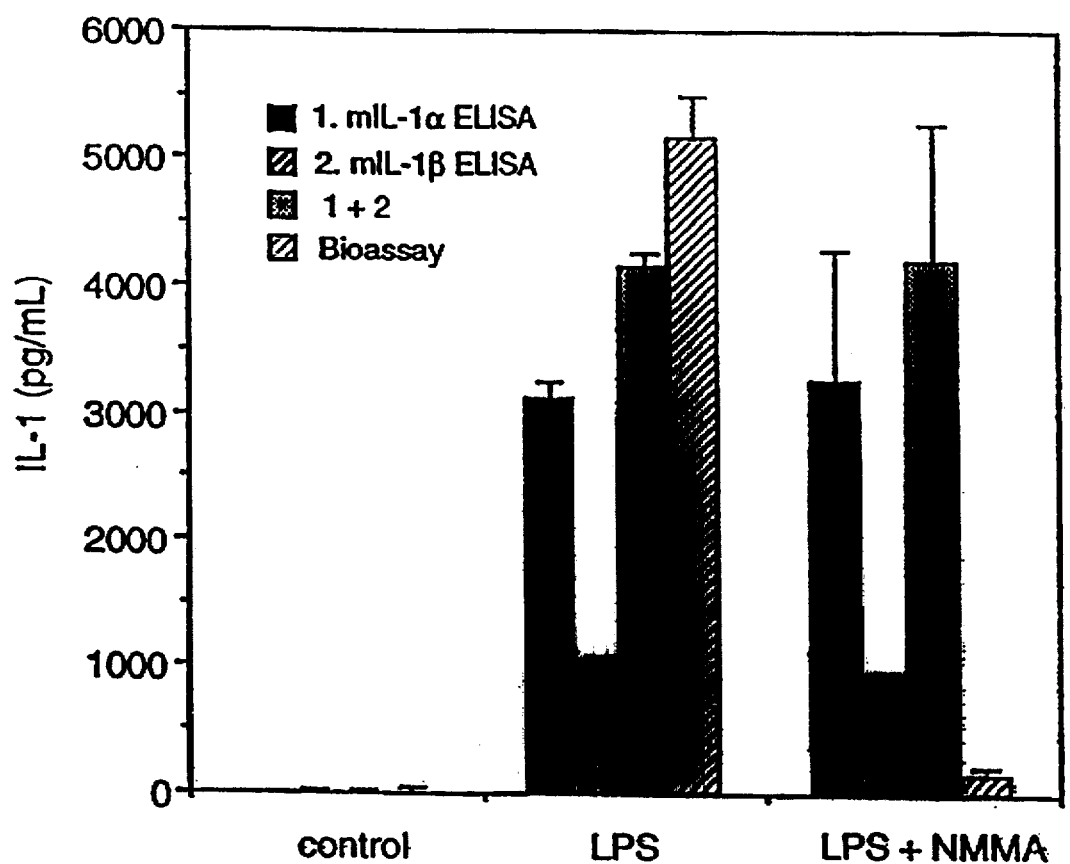
FIG. 5 illustrates the effects of NMMA and NO• on IL-1 protein released by LPS stimulated IL-1 producing cells as determined by an ELISA assay.

To test the possibility that the effect of NOS inhibition on LPS stimulated increases in IL-1 bioactivity was due to an action on the amount of protein released into the media, RAW264.7 cells were induced with LPS without and with NMMA (0.25 mM) and without and with SNAP (200 µM). The cells were stimulated as described in Example 1. The concentration of IL-1 protein released from LPS-stimulated RAW 264.7 cells was measured by ELISA using antisera specific for murine IL-1α and IL-1β. Murine IL-1α and IL-1β ELISA assays were performed on 1:10 and 1:50 dilutions of the cell free macrophage media according to the manufacturers' instructions (Genzyme). This method provides a direct measure of the amount of IL-1 specific protein released from LPS stimulated cells but does not distinguish between inactive and bioactive IL-1. The results in FIG. 5 are the average±SEM of six separate experiments containing three replicates per condition. Significant differences from IL-1α control are indicated by "*" (p<0.001) and by "$" (p<0.01) and differences from IL-1α levels of LPS+NMMA samples are indicated by "#" (p<0.05).

With reference to FIG. 5, RAW 264.7 cells stimulated in the presence of LPS for 24 hours significantly increased the amount of IL-1α released over control levels. NMMA addition to LPS activated cells inhibits IL-1α release which is reversed in the presence of the NO• donor, SNAP. Although there was a trend for an increase in the amount of IL-1β on LPS stimulation and an attenuation of IL-1β release on that increase in the presence of NMMA as well as a reversal on the attenuation by SNAP, these trends were not statistically significant.

EXAMPLE 7

This example illustrates the lack of effect of NMMA on the increase in amount of intracellular and released IL-1α, IL-1β and IL-1Ra upon LPS stimulation of murine macrophages.

Murine PEC cells were stimulated with LPS+ IFNγ±NMMA±SNAP and pulse/chase labeled with [$^{35}$S]-methionine (1000 Ci/mMol, Amersham Chemicals, Arlington Heights, Ill.). Murine PEC (1×10$^6$ cells) cells in MEM methionine-deficient media (9 parts MEM without methionine:1 part MEM containing methionine) were activated with LPS (1 µg/ml) and IFN-γ (150 u/ml)±NMMA (0.25 mM)±SNAP (200 µM) for 3 hours. The cells were then pulsed with 150 µCi [$^{35}$S]-methionine trans-label for 4 hours. The cells were washed with MEM to remove label, then NMMA and SNAP were replaced. The cells were incubated for an additional 17 hours (total incubation time was 24 hours). The supernatant was collected and cells were removed by centrifugation at 200×g for 1 minute. The labeled cells were washed in PBS and lysed in 0.15M NaCl, 1% nonidet plus protease inhibitors (aprotinin, 1 µg/ml; leupeptin, 1 µg/ml; PMSF, 0.1 mM; iodoacetamide, 1 mM; EDTA, 0.1 mM) by sonication and the lysates were clarified by centrifugation at 10,000×g for 30 minutes at 4° C. Protease inhibitors were also added to the supernatant. Both lysate and supernatant were precleared with 20 µl protein A sepharose (Sigma). Equivalent fractions of each sample were immunoprecipitated for 2 hours by addition of anti-murine IL-1α, anti-murine IL-1β or anti-human IL-1Ra (final dilutions 1:1000). Protein A sepharose was added for 1 hour and the beads were washed three times with PBS+1% nonidet+0.2% SDS and finally PBS and then boiled in SDS-PAGE sample buffer. Samples were resolved by 15% SDS-PAGE and visualized by fluorography.

Figure 6A:
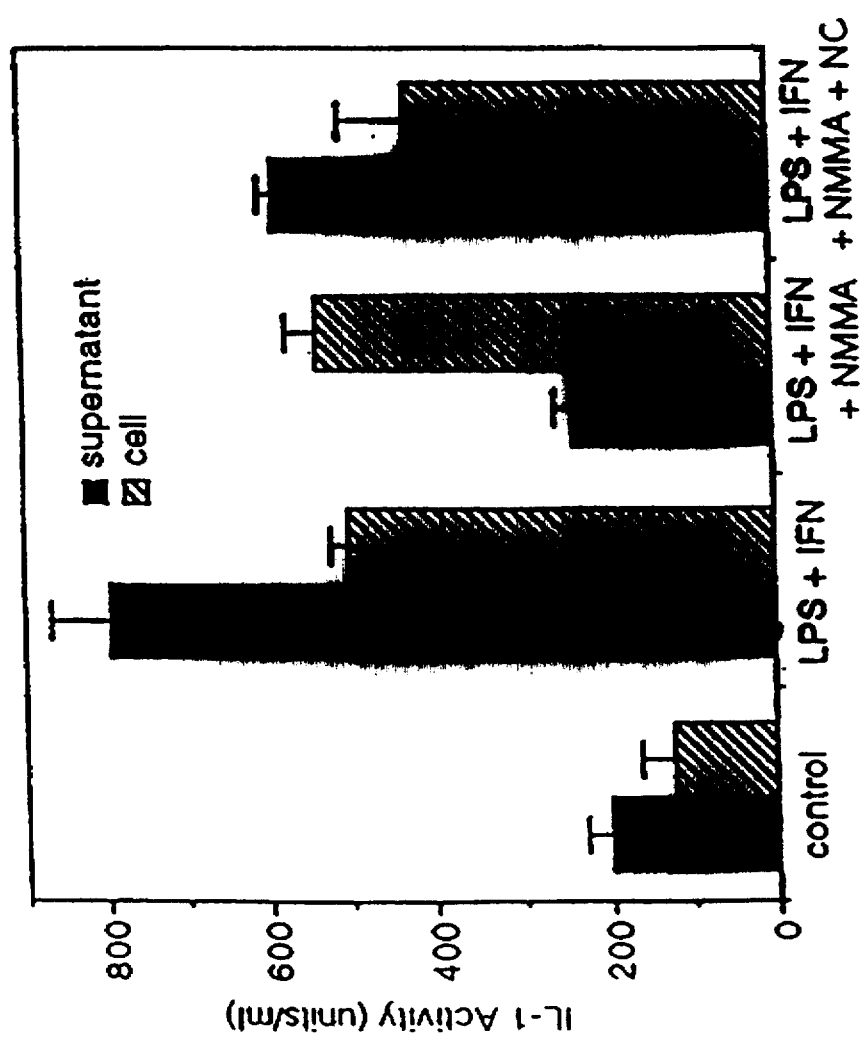
FIG. 6 illustrates (a) intracellular and extracellular IL-1 bioactivity in the absence or presence of NMMA and in the absence or presence of a NO• donor (b) immunoprecipitation of [$^{35}$S]-methionine labeled extracellular and intracellular LPS induced IL-1α, (c) immunoprecipitation of [$^{35}$S]-methionine labeled extracellular and intracellular LPS induced IL-1β, and (d) immunoprecipitation of [$^{35}$S]-methionine labeled extracellular and intracellular LPS induced IL-1Ra.
Figure 6B:
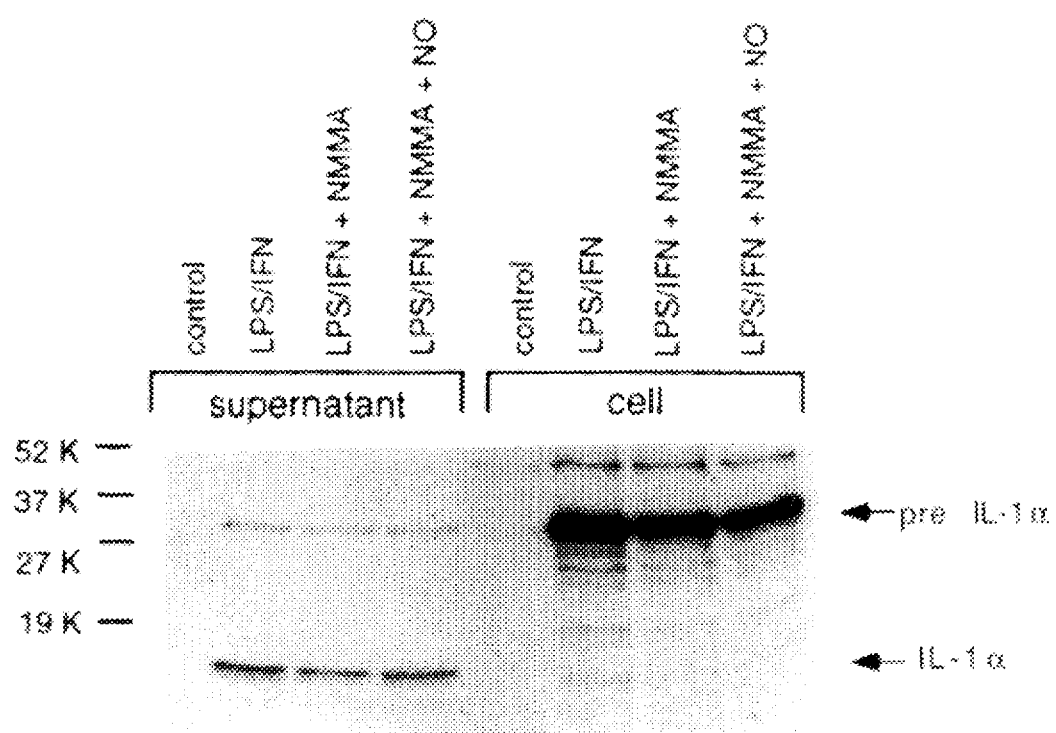
Figure 6C:
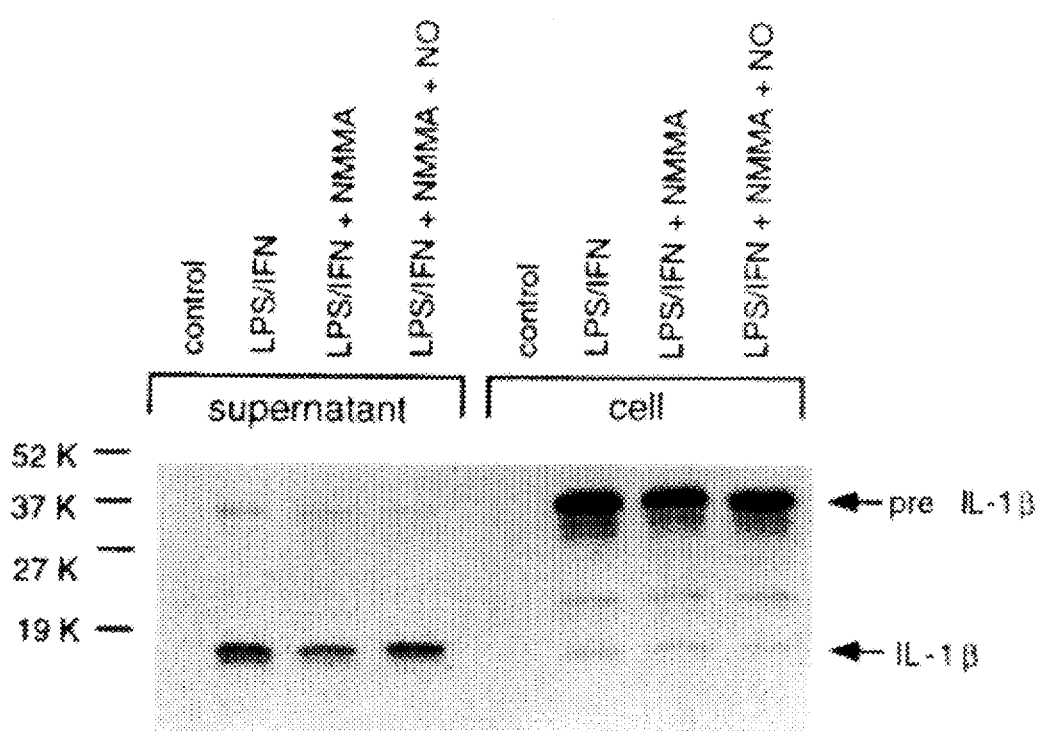
Figure 6D:
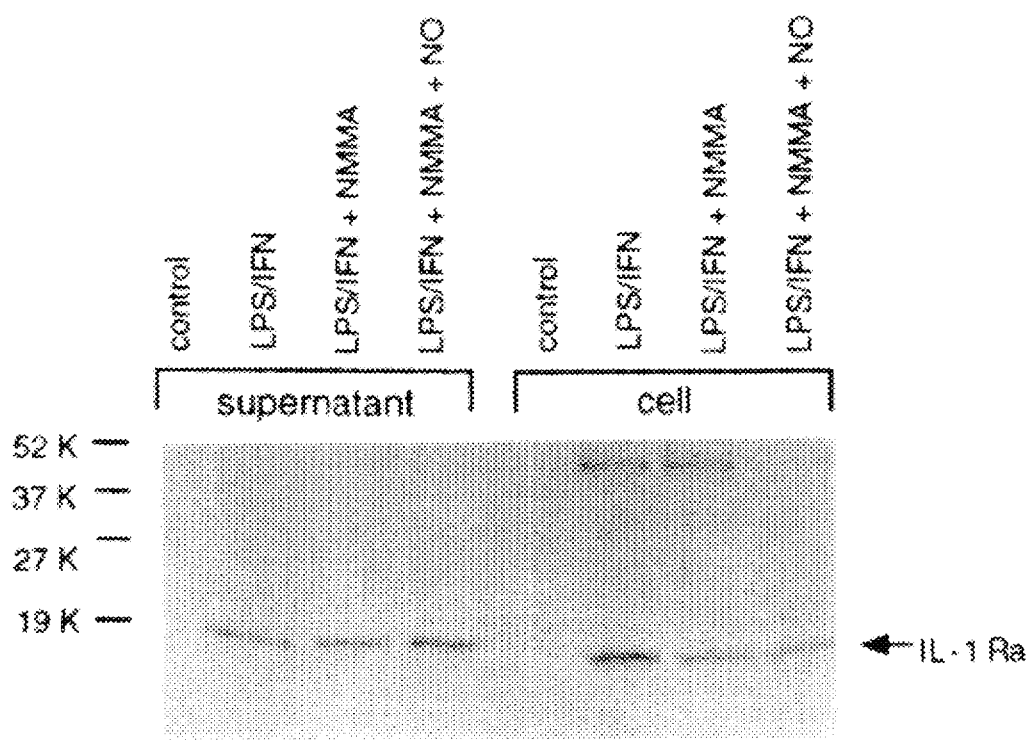

With reference to FIG. 6(a), cells and supernatant media were assayed for IL-1 bioactivity using the RINm5F assay as in Example 4. With reference to FIGS. 6(b), 6(c), and 6(d), samples prepared as described above were immunoprecipitated with antibodies specific for murine IL-1α, murine IL-1β, or human IL-1Ra. Bioactivity of intracellular and extracellular IL-1 was determined after LPS induction alone, or in the presence of NMMA with and without an added NO• donor (SNAP). FIG. 6(a) shows IL-1 bioactivity in the media is inhibited by NMMA and can be reconstituted with the NO• donor, SNAP, as was shown in Example 4. Immunoprecipitation of [$^{35}$S]-methionine labeled IL-1α and IL-1β showed that the major intracellular forms of these peptides are the uncleaved 33 kDa precursors (FIGS. 6b and 6c). The prevalent form found within the media was the processed 17.5 kDa protein. The results demonstrate that neither NMMA nor the NO• donor, SNAP, altered the predominant forms of the IL-1 proteins found in the cell or supernatant. Similarly the intracellular or released form of IL-1Ra elicited by LPS stimulation is not altered by NMMA or SNAP (FIG. 6d).

EXAMPLE 8

This example illustrates the role of cGMP antagonism in reversing the blocking effect of NMMA on LPS stimulated IL-1 bioactivity.

Figure 7:
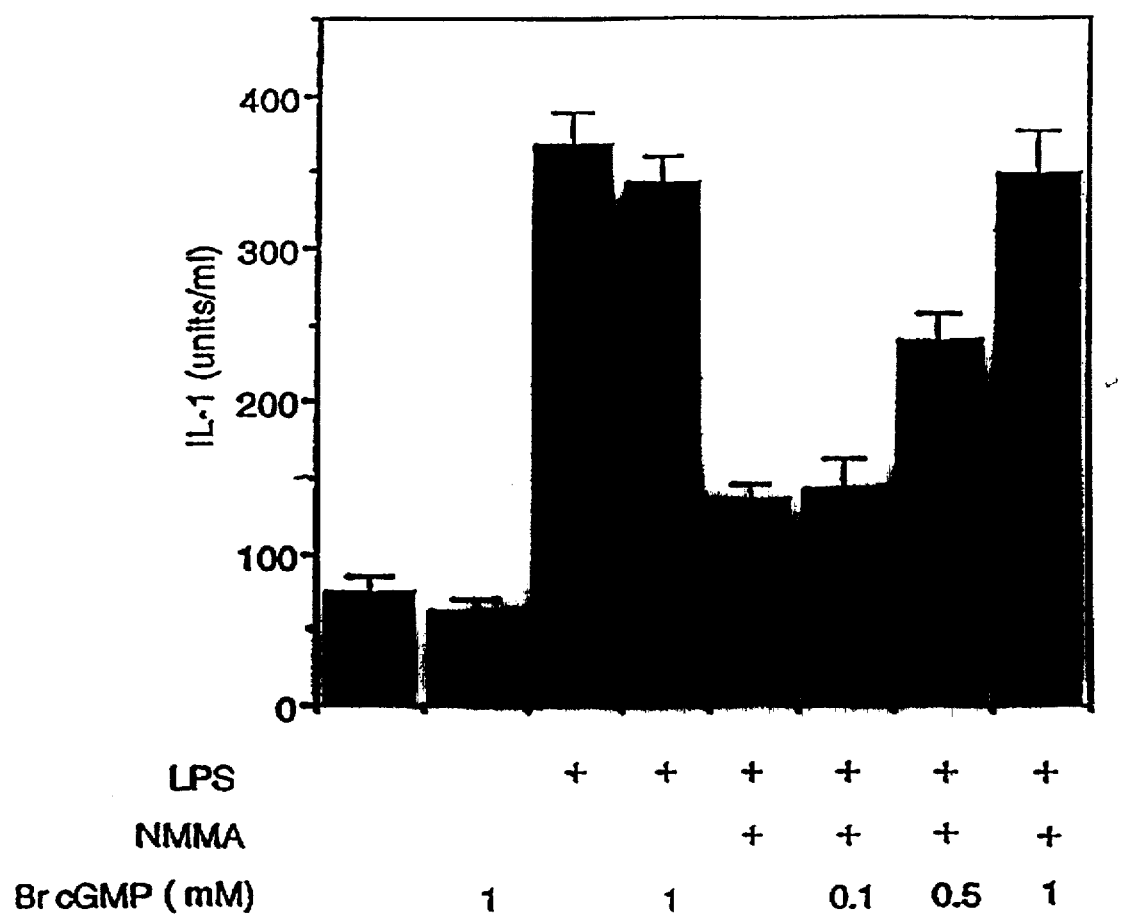
FIG. 7 illustrates the effect of 8-bromo-cGMP in reversing the NMMA inhibition of release of bioactive IL-1 from LPS stimulated IL-1 producing cells.

RAW264.7 cells were induced with 1 μg/ml LPS±0.25 mM NMMA for 24 hours as in Example 1. 8-Br-cGMP was added to the media for the final three hours of incubation. Media levels of IL-1 bioactivity were measured by the RINm5F bioassay as in Example 1. Results shown in FIG. 7 are the means±SEM of three separate experiments containing three replicates per condition. LPS stimulation increased IL-1 bioactivity and NMMA inhibited this increase as shown earlier. The addition of 8-Br-cGMP blocked this inhibition by NMMA in a concentration dependent manner over the concentration range of 0.1 to 1.0 mM. This result suggests that NO• may mediate bioactive IL-1 release by a cGMP dependent mechanism.

EXAMPLE 9

This example illustrates the effect of NMMA in blocking LPS stimulated IL-1 bioactivity in the RINm5F and thymocyte bioassays.

Figure 8:
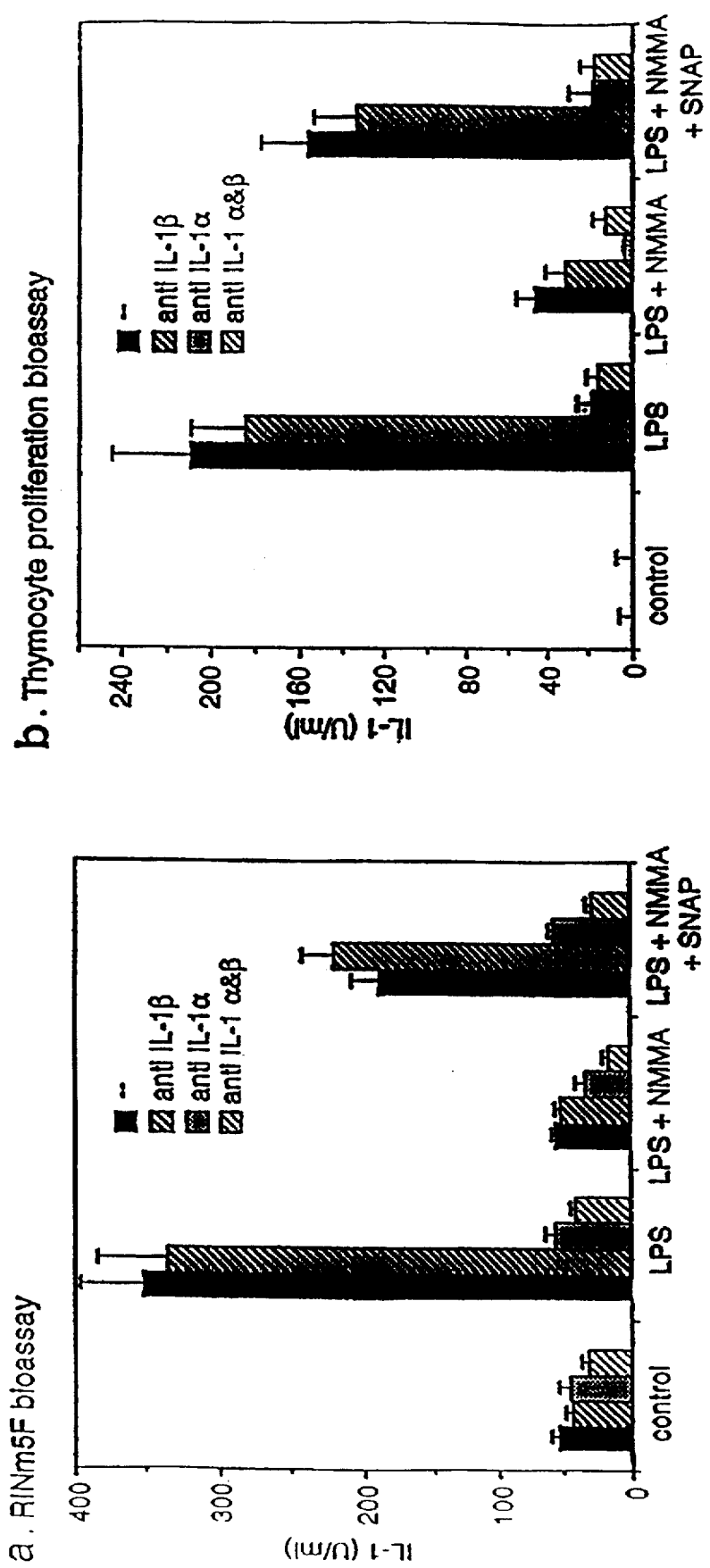
FIG. 8 illustrates a comparison of assays measuring bioactive IL-1 release from LPS stimulated RAW264.7 cells (a) in a RINm5F bioassay and (b) in a thymocyte proliferation bioassay before and after pretreatment with IL-1 specific antibodies.

RAW264.7 cells were activated by 1 μg/ml LPS±0.25 mM NMMA±SNAP for 24 hours and the media was assayed for IL-1 bioactivity in the RINm5F bioassay and the thymocyte proliferation bioassay as described in Example 1. To distinguish between bioactivity arising from IL-1α or IL-1β, RAW264.7 cell free media was preincubated with 1 μg/ml anti-IL-1α, anti-IL-1β or both for 30 minutes at 4° C. prior to each bioactivity assay. Results shown in FIG. 8 are the mean±SEM of three separate experiments containing three replicates per condition.

The ability to stimulate release of bioactive IL-1 was confirmed by both assays. Both the RINm5F bioassay (FIG. 8a) and thymocyte proliferation bioassay (FIG. 8b) showed a 10-fold increase in IL-1 bioactivity released by LPS-stimulated RAW264.7 cells over control levels. The increase in bioactivity was significantly inhibited by NMMA and this inhibition was overcome by addition of the NO• donor, SNAP. Pretreatment with anti-IL-1α and anti-IL-1β antibodies abolishes bioactivity in both assays, while anti-IL-1α antibodies alone block more than 90% of the measured bioactivity, and anti-IL-1β antibodies have little effect. These results suggest that most of the measured IL-1 bioactivity released from LPS stimulated RAW264.7 cells is due to IL-1 α.

EXAMPLE 10

This example illustrates the effects of NOS inhibitors on the release of bioactive IL-1 produced by stimulation with LPS and PMA in human monocytes.

Two different experiments were designed to test the effect of NOS inhibitors in blocking the release of bioactive IL-1 from human monocytes. In one experiment, human monocytes were obtained from heparinized whole blood by venipuncture of normal adult volunteers and isolated by density gradient centrifugation on Histopaque-1077 (Sigma Chemical Company, St. Louis, Mo.). Purified monocytes were obtained by counterflow centrifugal elutriation (CCE). The resulting cell population was always greater than 98% monocytes as determined by LeukoStat cytospin stain (Fisher Scientific, Pittsburgh, Pa.). Purified human monocytes (1×10$^6$ cells/ml) in complete CMRL were activated for 24 hours at 37° C. in 95% air, 5% CO$_2$ with 10 μg/ml LPS+50 ng/ml PMA in the presence of 0.5 mM NMMA, 0.5 mM aminoguanidine (AG), 0.5 mM L-N6-(1-iminoethyl)-lysine (NIL), or 1 μM iodonium diphenyl (ID). Cell free supernatants were assayed for IL-1 bioactivity in a RINm5F bioassay. In another experiment, human premonocytic U937 cells were obtained from American Type Tissue Culture and grown to confluency in RPMI supplemented with 15% heat-inactivated fetal bovine serum, 2 mM glutamine and 0.1 mM non-essential amino acids. The cells were plated at 2×10$^5$ cells/200 μl in complete CMRL for 24 hours prior to activation. U937 cells (1×10$^6$ cells/ml) were stimulated with 10 μg/ml LPS+50 ng/ml PMA for 72 hours in the presence of NOS inhibitors at concentrations ranging from 0.05 to 0.5 mM for NMMA, AG and NIL, and from 0.05 to 1.0 μM for ID. Supernatants were assayed for IL-1 bioactivity in RINm5F bioassays as described above. To determine whether residual NOS inhibitors did not affect the bioassay, NOS inhibitors were added to unstimulated cells at identical concentrations as added to stimulated cells. Aliquots of the unstimulated cells with NOS inhibitors were added to RINm5F cells at equivalent dilutions to the stimulated cells at dilutions of 1:50 and 1:100 following incubation. Human IL-1β (0.5 U/ml) was then added to the RINm5F cells and the resulting nitrite levels were compared to aliquots without NOS inhibitors. No difference in nitrite levels was observed, indicating that the low concentration of NOS inhibitors carried over does not affect NO• production by RINm5F cells, similar to observations in Example 1 above. Results shown in FIGS. 9a and 9b are means±SEM of four separate experiments containing three replicates per condition.

Figure 9:
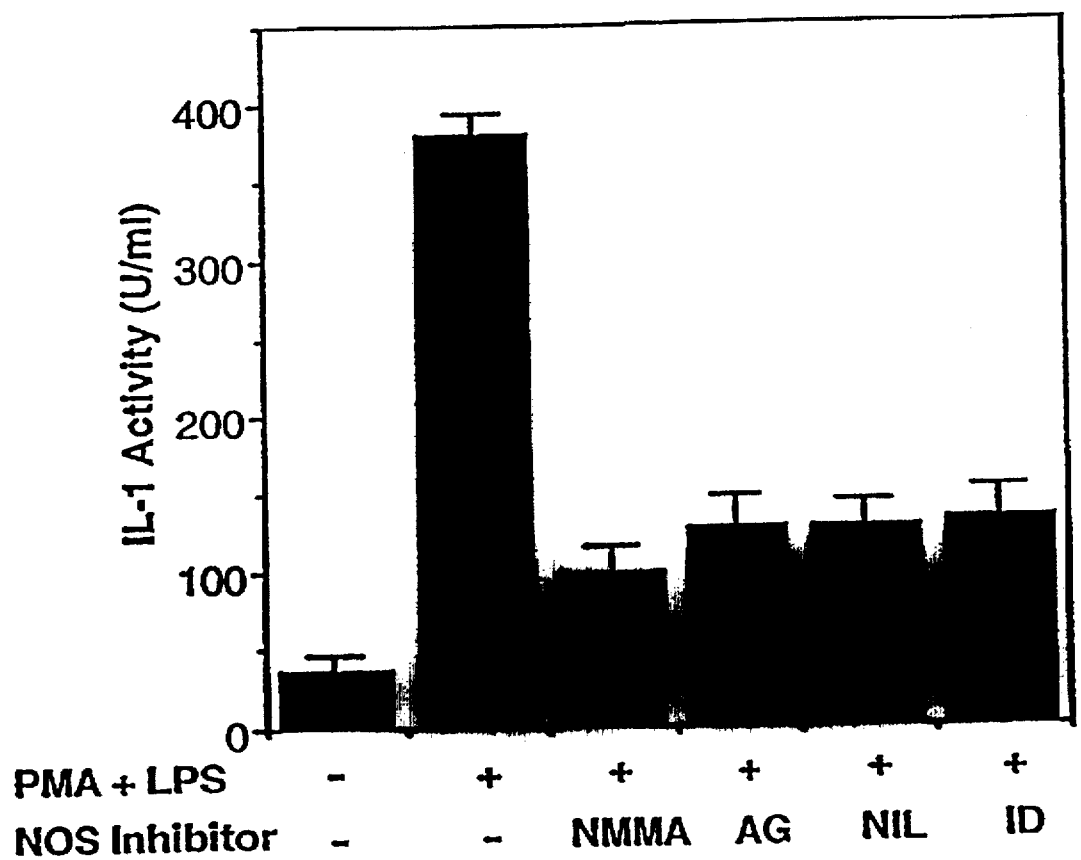
FIG. 9 illustrates the effects of NOS inhibitors on (a) the release of bioactive IL-1 from human monocytes stimulated with LPS and PMA and (b) the dose dependent inhibition by NOS inhibitors on bioactive IL-1 released from stimulated human monocytic cells, U937.
Figure 9:
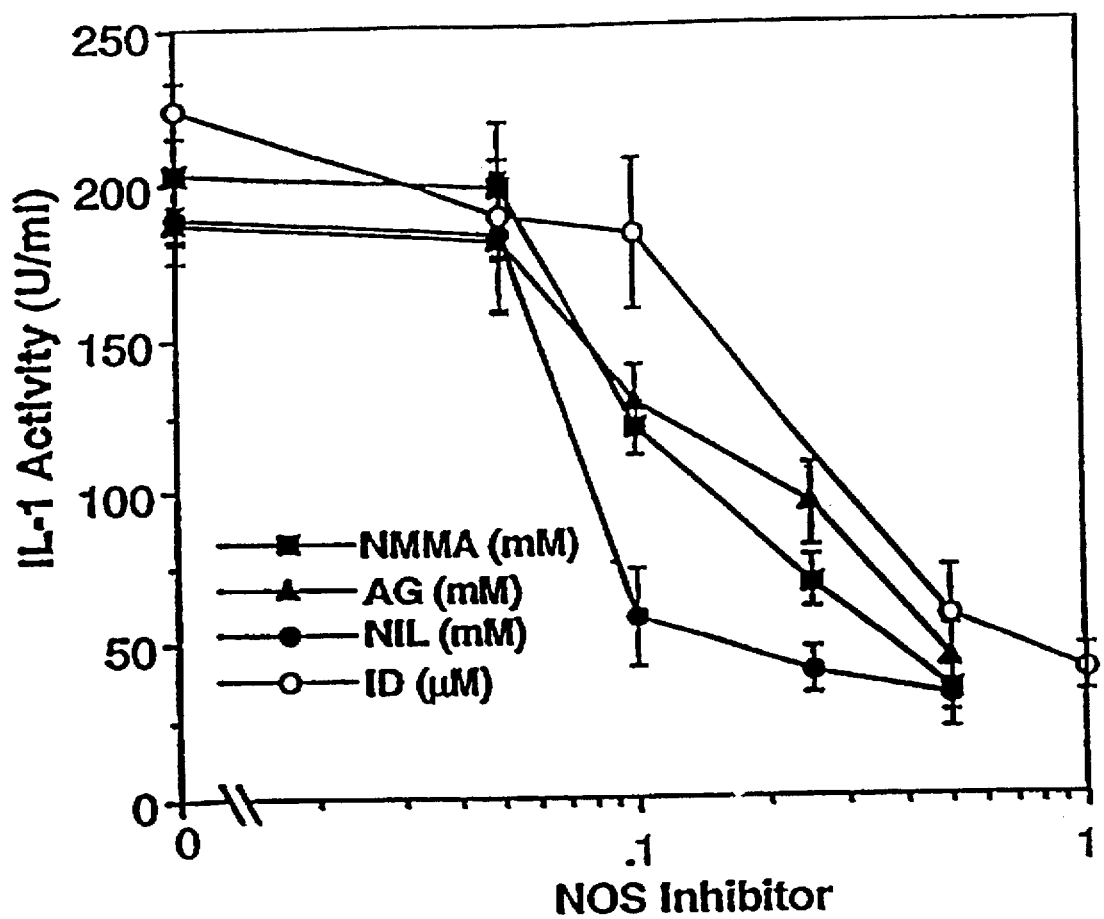

As shown in FIG. 9, human monocytes activated with LPS and PMA produced a 10-fold increase in bioactive IL-1 released into the medium. The NOS inhibitors, aminoguanidine, NMMA, NIL and ID significantly diminished the IL-1 bioactivity released by primary monocytes (FIG. 9a). The same NOS inhibitors showed a concentration effect in diminishing IL-1 released from U937 human monocytic cells (FIG. 9b).

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method for inhibiting IL-1 bioactivity in a individual afflicted with a condition resulting from IL-1 bioactivity released from IL-1 producing cells comprising administering an inhibitory effective amount of aminoguanidine wherein said condition is acute hypotension or acute hypoglycemia induced by endotoxic shock, acute myeloblastic leukemia, chronic myelogenous leukemia, chronic juvenile gramulocytic leukemia, progressive degenerative effects of Alzheimer's disease, neuropathological changes in Down's syndrome, or bone degeneration due to estrogen deficiency.

2. The method according to claim 1 wherein aminoguanidine is administered in a pharmaceutically acceptable formulation.

3. The method according to claim 2 wherein the aminoguanidine is administered orally.

4. The method according to claim 2 wherein the aminoguanidine is administered parenterally.

5. The method according to claim 4 wherein the aminoguanidine is administered intravenously or subcutaneously.

* * * * *